US00PP22568P2

(12) United States Plant Patent
Jansen

(10) Patent No.: US PP22,568 P2
(45) Date of Patent: Mar. 6, 2012

(54) ***PENSTEMON* PLANT NAMED 'BLUEBERRY TAFFY'**

(50) Latin Name: ***Penstemon* spp.**
Varietal Denomination: Blueberry Taffy

(75) Inventor: Robert D. Jansen, Beaverton, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/927,576

(22) Filed: Nov. 17, 2010

(51) Int. Cl.
*A01H 5/00* (2006.01)

(52) U.S. Cl. ..... Plt./465

(58) Field of Classification Search ..... Plt./465
See application file for complete search history.

*Primary Examiner* — Annette Para
(74) *Attorney, Agent, or Firm* — Jondle & Associates, P.C.

(57) ABSTRACT

A new and distinct cultivar of *Penstemon* plant characterized by large purple blue flowers with a dark maroon ring at the base of the lobes and white tube, dense flower clusters, long bloom time, a compact, upright, well branched habit, with multiple crown from the base, clean-looking, deep green, attractive foliage, and excellent vigor.

1 Drawing Sheet

Botanical denomination: *Penstemon* spp.
Variety designation: 'Blueberry Taffy'.

BACKGROUND OF THE INVENTION

The present invention relates to a new and distinct cultivar of *Penstemon*, given the name, 'Blueberry Taffy'. *Penstemon* is in the family *Scrophulariaceae*. This plant originated from an open pollinated cross using *Penstemon* 'Raspberry Flair', an unpatented plant, as the seed parent. This cultivar was selected for its compact growing habit, large flowers in dense clusters, long flowering time, vigor, and clean attractive look. It is an ideal plant for a sunny border in full sun.

Compared to the seed parent, *Penstemon* 'Raspberry Flair', an unpatented plant, the new cultivar has purple blue flowers rather than raspberry pink, a much longer bloom time, longer inflorescences, and more stems from the crown.

*Penstemon* 'Blueberry Taffy' is uniquely distinguished by its:

1. large purple blue flowers with a dark maroon ring at the base of the lobes and white tube,
2. dense flower clusters,
3. long bloom time,
4. compact, upright, well branched habit, with multiple crown from the base,
5. clean-looking, deep green, attractive foliage,
6. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a close up of a one year old *Penstemon* 'Blueberry Taffy' in the summer in Canby, Oreg.

FIG. 2, foreground, shows a two year old *Penstemon* 'Blueberry Taffy' in bloom growing in full sun in the trail bed in July in Canby, Oreg.

DETAILED PLANT DESCRIPTION

The following is a detailed description of the new *Penstemon* cultivar based on observations of one and a half year-old specimens grown outside in the ground in the garden in Canby, Oreg. in mid August. The color descriptions are all based on The Royal Horticultural Society Colour Chart, 5$^{th}$ edition.

Plant:

*Type*.—Herbaceous perennial.
*Form*.—Upright, branching.
*Cold hardiness*.—USDA Zone 7-10.
*Size*.—Grows to 56 cm wide and 56 cm high.
*Vigor*.—Excellent.
*Stem number*.—About 10 stems from the crown.
*Stem*.—Upright, grows to 36 cm long and 5 mm wide (at the base), glabrous, internodes grow to 5 cm long, Yellow Green 145C.
*Rooting*.—Plants root easily from stem cuttings.

Leaf:

*Type*.—Simple.
*Arrangement*.—Opposite.
*Shape*.—Lanceolate.
*Venation*.—Pinnate.
*Margins*.—Denticulate.
*Apex*.—Acuminate.
*Base*.—Sessile.
*Blade size*.—Grows to 12 cm long and 2.6 cm wide.
*Surface texture*.—Glabrous on both sides.
*Leaf color*.—Topside Green 137A, bottom side Green 137B.

Inflorescence:

*Type*.—Terminal, many flowered, dense thyrse.
*Number of flowers per inflorescence*.—26 on average.
*Size of inflorescence*.—Grows to 28 cm long and 10 cm wide.
*Peduncle*.—Grows to 4 cm long and 4 mm wide, pubescent, Yellow Green 145B.

*Pedicel*.—Grows to 10 cm long and 1 mm wide, pubescent, Yellow Green 147C.

*Bloom period*.—Mid June to frost in October in Canby, Oreg.

Flower bud:

*Size*.—3 cm long and 15 mm wide.

*Description*.—Closed tubular, bulging, flattened ventrically.

*Color*.—White 155A except Violet 83B on lobes.

Flower:

*Type*.—Zygomorphic, perfect.

*Shape*.—Tubular, bilabiate.

*Size*.—Grows to 4.5 cm long and 3.8 cm wide.

*Corolla description*.—Grows to 4.5 cm long and 3.8 cm wide; tube is funnel-form in the calyx for 6 mm long and 5 mm wide, inflating for 25 mm long to 15 mm wide, flaring into 5 lobes, the two smaller top lobes flare back (15 mm wide and 10 mm deep) and two larger lateral lobes flare out (15 mm wide and 15 mm deep), and the lower lobe flares down (15 mm wide and 10 mm deep), lobe margins entire, tips obtuse; outside pubescent, inside glabrous; outside Purple Violet N81A on bottom of funnel to White NN155B on funnel to Violet 86C and N87B on lobe backs; inside color is Violet 86B on lobes outer ¾, 3 bottom lobes have a ring of Purple N79C which extends up their main veins and in lines of bee tracks down the funnel, tube is White NN155D.

*Calyx description*.—10 mm deep and 7 mm wide, 5 overlapping lobes cut to the base, each lobe broadly ovate in shape, 9 mm deep and 5 mm wide, margins entire, tip acute, base cuneate, Yellow Green 146C, glabrous inside and pubescent outside.

*Pistil description*.—1, 24 mm long, ovary 5 mm long and 3 mm wide, Yellow Green 145A; style 18 mm long and less than 1 mm wide, stigma and style White NN155C.

*Stamen description*.—5, one sterile without an anther, held within the corolla, filaments 22 to 32 mm long and White NN155C, anthers 3 mm wide and 2 mm deep, Greyed Purple N186D, pollen White NN155C.

*Fragrance*.—None.

*Lastingness*.—A flower lasts 5 to 6 days.

Fruit:

*Type*.—Capsule.

*Fertility*.—Good.

*Size*.—1.2 cm deep and 4 mm wide.

*Color*.—Brown 200A to B.

Seed:

*Shape*.—Irregular.

*Size*.—2 mm long.

*Color*.—Brown 200A.

Pests and diseases:

Excellent disease tolerance to root rot, a common problem for *Penstemon*. Leaf spot, rust, and powdery mildew may be a problem, but have not been observed on the new cultivar. No known disease or pest resistances.

I claim:

1. A new and distinct cultivar of *Penstemon* plant substantially as shown and described.

* * * * *

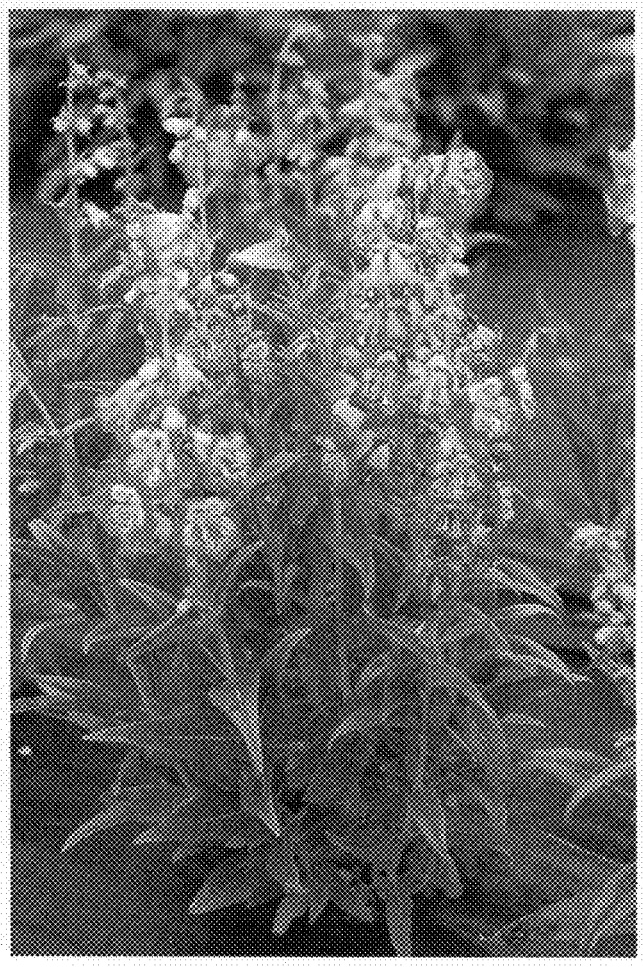

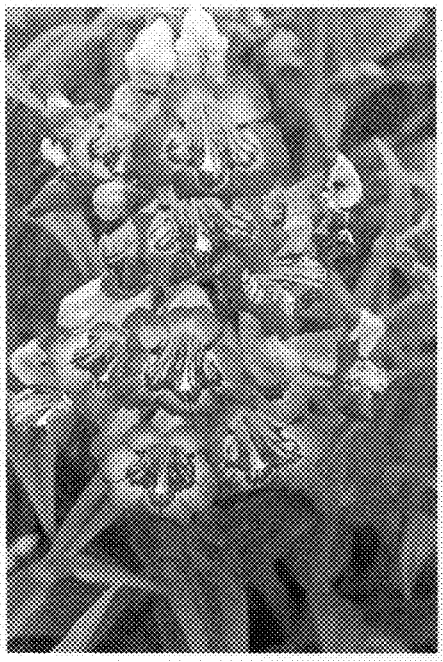
Figure 1 to left
Figure 2 below